United States Patent [19]

Abrams et al.

[11] Patent Number: 5,171,563
[45] Date of Patent: Dec. 15, 1992

[54] CLEAVABLE LINKERS FOR THE REDUCTION OF NON-TARGET ORGAN RETENTION OF IMMUNOCONJUGATES

[75] Inventors: Paul G. Abrams, Seattle; John M. Reno, Brier; Alan R. Fritzberg, Edmonds; Ananthachari Srinivasan, Kirkland; David C. Anderson, Seattle, all of Wash.

[73] Assignee: NeoRx Corporation, Seattle, Wash.

[21] Appl. No.: 830,973

[22] Filed: Feb. 10, 1992

Related U.S. Application Data

[63] Continuation of Ser. No. 251,900, Sep. 30, 1988, abandoned.

[51] Int. Cl.$^5$ ............... A61K 49/02; A61K 49/00; A61K 37/00; A61K 39/395
[52] U.S. Cl. ..................... 424/1.1; 424/9; 424/4; 424/7.1; 424/85.91; 424/94.63; 424/94.64; 424/717; 424/720; 514/474; 514/562; 514/836; 514/922; 530/391.1; 530/391.5; 530/391.9; 530/402; 530/807
[58] Field of Search ............ 424/1.1, 85.91, 9, 94.63, 424/94.64, 717, 720, 4, 7.1; 530/391.1, 391.5, 391.9, 402, 807; 514/922, 836, 474, 562

[56] References Cited

U.S. PATENT DOCUMENTS

| | | | |
|---|---|---|---|
| 4,081,246 | 3/1978 | Polito et al. | 424/1.1 X |
| 4,110,432 | 8/1978 | Wilkinson et al. | 424/85.8 |
| 4,232,119 | 11/1980 | Carlsson et al. | 530/390 X |
| 4,340,535 | 6/1982 | Voisin et al. | 530/390 X |
| 4,511,501 | 4/1985 | Luduena | 530/408 |
| 4,569,789 | 2/1986 | Blattler et al. | 530/391.9 |
| 4,625,014 | 11/1986 | Senter et al. | 424/85.91 X |
| 4,631,190 | 12/1986 | Shen et al. | 424/85.91 X |
| 4,643,895 | 2/1987 | Casellas et al. | 424/85.91 |
| 4,647,671 | 3/1987 | Schwartz | 424/1.1 X |
| 4,671,958 | 6/1987 | Rodwell et al. | 424/85.91 |
| 4,698,420 | 10/1987 | Urnovitz | 530/389 X |
| 4,849,511 | 7/1989 | Verbruggen | 534/14 |
| 4,867,962 | 9/1989 | Abrams | 424/1.1 |
| 4,867,973 | 9/1989 | Goers et al. | 530/391 X |
| 4,888,415 | 12/1989 | Lambert et al. | 530/390 |
| 4,952,394 | 8/1990 | Senter | 424/85.91 |
| 4,981,979 | 1/1991 | Sivam | 530/391 X |
| 4,997,913 | 3/1991 | Hellstrom et al. | 530/389 |

FOREIGN PATENT DOCUMENTS

| | | | |
|---|---|---|---|
| 031999 | 7/1981 | European Pat. Off. | 424/85.91 |
| 044167 | 1/1982 | European Pat. Off. | 424/85.91 |
| 063988 | 11/1982 | European Pat. Off. | 424/85.91 |
| 115171 | 12/1982 | European Pat. Off. | |
| 0317957 | 5/1989 | European Pat. Off. | |
| 67433 | 4/1985 | Japan . | |
| 8912624 | 12/1989 | PCT Int'l Appl. | 424/85.91 |

OTHER PUBLICATIONS

International Search Report for International Application No. PCT/US89/04266.
Meares et al, *Intl. J. Cancer [Suppl]* (United States) 1988, 2 pp. 99–102, "Chelate Radiochemistry: cleavable linkers lead to altered levels of radioactivity in the liver".
Blakely et al, *Antibody, Immunoconjugates, and Radiopharmaceuticals*, vol. 1, Nov. 1, 1988, pp. 1–16, "An Overview of Therapy with Immunotoxins Containing Ricin or Its A–Chain".
Deshpande et al, *Int. J. Rad. Appl. Instrum.* [B] (England) 1989, 16 (6) pp. 587–597, "Effect of Different Linkages Between Chelates and Monoclonal Antibodies on Levels of Radioactivity in the Liver".
Haseman et al, *European J. Nucl. Med.* (1986) 12:455–460, "Metabolizable 111 In chelate conjugated anti–idiotype monoclonal antibody for radioimmunodetection of lymphoma in mice".
Bundgaard et al, *J. Med. Chemistry*, 1987, 30, pp. 451–454, "Esters of N,N–Disubstituted 2–Hydroxyacetamides as a Novel Highly Biolabile Prodrug Type for Carboxylic Acid Agents".
Blattler et al, *Biochemistry*, 1985, 24, 1517–1524, "New Heterobifunctional Protein Cross-Linking Reagent That Forms an Acid-Labile Link".
Worrell et al, *Anti-Cancer Drug Design* (1986), 1, pp. 179–188, "Effect of Linkage Variation on Pharmacokinetics of Ricin A Chain-Antibody Conjugates in Normal Rats".
Goodwin et al, *J. Nucl. Med.* (Jun., 1986) vol. 27, No. 6, p. 959, Abstract 336.
Quadri et al, *J. Nucl. Med.* (Jun., 1986) vol. 27, No. 6, p. 959, Abstract 337.
Goodwin et al, *Nucl. Med. Biol.* (1986) vol. 13, NO. 4, pp. 383–391, "Monoclonal Antibodies as Reversible Equilibrium Carriers of Radiopharmaceuticals".

Primary Examiner—Robert L. Stoll
Assistant Examiner—John M. Covert
Attorney, Agent, or Firm—Millen, White, Zelano and Branigan

[57] ABSTRACT

A process for reducing the non-target organ accumulation of immunoconjugates administered in vivo during therapeutic or diagnostic procedures involves the use of immunoconjugates comprising linkers that are cleavable at the non-target organs. The linkers are cleavable under conditions present, or induced, at one or more non-target organs, which include the kidneys or the liver.

34 Claims, No Drawings

CLEAVABLE LINKERS FOR THE REDUCTION OF NON-TARGET ORGAN RETENTION OF IMMUNOCONJUGATES

This application is a continuation of application Ser. No. 07/251,900, filed Sep. 30, 1988, now abandoned.

TECHNICAL FIELD OF THE INVENTION

This invention relates to a method for the reduction of non-target organ accumulation of diagnostic and therapeutic agents that are delivered to non-target as well as target sites in the form of immunoconjugates. The method uses linkers in the immunoconjugates that cleave in response to certain conditions at the non-target organ, including enzymatic activity or a change in environment such as pH, redox couple, or reducing conditions.

BACKGROUND OF THE INVENTION

There has been considerable interest in the development of conjugates comprising various diagnostic or therapeutic agents attached to targeting proteins, such as antibodies. Recent efforts have included the conjugation of diagnostic, cytotoxic or anti-neoplastic agents to specific antibodies such as monoclonal antibodies to produce conjugates which can selectively target tumor cells while sparing normal tissues.

A large number of different classes of active agents have been considered, including diagnostic radioisotopes, beta and alpha emitting therapeutic radioisotopes, plant and bacterial toxins, and a variety of anti-neoplastic drugs including intercalating agents, antimetabolites, alkylating agents and antibiotics.

In spite of the advantages achieved by attaching active agents to targeting proteins, problems associated with localization of the conjugates on non-target organs remain. Targeting proteins such as antibodies are rarely totally specific for the desired target tissue, and conjugates comprising targeting proteins therefore frequently localize on non-target tissues through such mechanisms as cross-reactive binding, non-specific uptake, or excretory handling.

For example, one problem with the administration of radioimmunoconjugates used for diagnostic imaging, especially an immunoconjugate comprising a radionuclide imaging agent and an antibody fragment, is the tendency for radioactivity to localize nonspecifically in the kidney. This results in the kidney region frequently showing up on the image scans. Accordingly, a means for selectively removing the localized immunoconjugates from the kidney region without decreasing the radioactivity at the target site would be helpful for augmenting the clarity of diagnostic images. Further, an immunoconjugate comprising a therapeutic radionuclide moiety and an antibody fragment as the targeting protein generally will also localize in the kidney, potentially exerting undesirable renal toxicity and thereby lowering the therapeutic index of the immunoconjugate. Indeed, the kidney may be the limiting organ of toxicity, preventing administration of larger, more efficacious doses of radionuclide.

Other problems can develop when an immunoconjugate tends to localize in the liver. The liver occupies a large area in the abdomen, and localization of diagnostic immunoconjugates at the liver can mask other target sites where the immunoconjugate may have also localized, and obscure metastatic lesions. When a therapeutic immunoconjugate localizes in the liver, the liver tissue is exposed to the toxic effects of the therapeutic agent.

Efforts to effect clearance of radionuclide chelates that are not bound to target tissues in vivo have included the administration of immunoconjugates comprising radionuclide chelates attached to antibodies through certain linkers that are potentially cleavable under conditions present within the body. These potentially "metabolizable" linkers include certain linker molecules comprising thiourea groups, peptides, esters, or disulfides. See, for example, Quadri et al., (*J. of Nuc. Med.*, Vol. 27, No. 6, p 959, Abstract No. 337, June 1986), Haseman et al. (*J. Nucl. Med.* 12:455-460 [1986]), and Meares et al. (*Int. J. Cancer* [Suppl.] U.S., Vol. 2, pp. 99-102[1988]).

Clearance of the radioisotope from the host's body (which is believed to be due to cleaving of the linker to release the chelate from the antibody) was analyzed. Clearance of radionuclides from the body generally was enhanced to various degrees, compared to immunoconjugates comprising non-cleavable linkers. When comparative studies were conducted, disulfide bonds generally were found to be more susceptible to cleavage in vivo than the other linkages described above. In fact, conventional disulfide linkers have been found to be too labile in many cases, with the chelates being released from the antibody so quickly that insufficient amounts of the immunoconjugates reached the target site. Much room for improvement remains with respect to the use of cleavable linkers to release chelates from immunoconjugates.

A need remains for methods of reducing localization of targeting protein conjugates comprising diagnostic or therapeutic agents on non-target tissues. Removing these agents from non-target organs will improve the clarity of diagnostic images and will reduce the exposure of non-target tissues to cytotoxic agents.

SUMMARY OF THE INVENTION

The problems associated with non-target organ retention of conjugates comprising targeting proteins (e.g., immunoconjugates) may be reduced by a process which removes non-target organ localized diagnostic or therapeutic agents. Frequent non-target organs of immunoconjugate localization are the liver and excretion organs, i.e., the kidney and the hepatobiliary system that releases it into the intestine.

The present invention provides a method for selectively reducing non-target organ accumulation of an effector moiety, (i.e., a diagnostic or therapeutic agent). The method comprises administering to a human or mammalian host a conjugate comprising an effector moiety attached to a targeting protein through a linker and administering to the host a cleaving agent that effects cleavage of the linker at one or more non-target sites within the host. Thus, a process for selectively removing accumulated effector moieties from non-target tissue by cleaving the linker attaching the effector moiety of the conjugate to the targeting protein is provided. This will allow for the elimination of the previously non-target tissue bound effector moiety from the host's body, while permitting the relative retention of the effector moiety at target sites. The cleaving agent may effect cleavage of the linker by selectively changing the tissue or cellular environment of the non-target tissue having accumulation of the immunoconjugate therein, e.g., in terms of the pH, reducing environment, oxidizing environment, or enzyme exposure. The change in the conditions present at the non-target tissue promotes cleavage of the particular linker chosen for use. Examples of cleaving agents include, but are not limited to, enzymes, compounds that raise or lower the pH at a non-target site, and reducing agents.

The linker equilibrium at the cleavage site shifts to cleavage with an induced change in the tissue or cellular environment at one or more non-target organs. The cleavage of the linker binding the effector moiety to the targeting protein of the conjugate in accordance with the present invention allows for selective removal of the effector moiety from non-target organs. Conjugates comprising diagnostic or therapeutic agents attached to targeting proteins through linkers cleavable under conditions present or induced at a particular non-target site are also provided.

DETAILED DESCRIPTION OF THE INVENTION

The present invention provides a method for reducing non-target organ accumulation of an effector moiety, comprising administering to a human or mammalian host a conjugate comprising an effector moiety attached to a targeting protein through a linker that is selectively cleaved at one or more non-target sites within the host. A cleavable linker chosen for use in the present invention will cleave in response to certain predetermined environmental conditions or predefined changes in the environmental conditions to effect a selective cleavage of immunoconjugates comprising these linker groups that are exposed to this tissue or cellular environmental change or condition. Changes in such conditions may be induced by administering an appropriate cleaving agent to the host, as discussed below.

The linker connects an effector moiety to a targeting molecule, usually peptides or proteins. The effector moiety is a diagnostic or therapeutic agent. Examples of diagnostic agents are diagnostic radionuclides, nuclear magnetic resonance contrast agents, X-ray contrast agents, and other imaging agents. Therapeutic agents include, but are not limited to, therapeutic radionuclides and drugs such as cytotoxic drugs (including anti-cancer drugs). The type of therapeutic agent chosen for use will vary according to the nature of the patient's illness. The radionuclides may be in the form of a stable complex such as a chelate. Preferably, the chelate is a molecule that is rapidly excreted in the urine if administered in its free form.

The targeting molecule binds to a desired target site in vivo. The targeting molecules may bind to a receptor, substrate, antigenic determinant, or other binding site on a target cell or tissue. Examples of targeting proteins include, but are not limited to, antibodies, enzymes (e.g., fibrinolytic enzymes), biologic response modifiers (e.g., interleukins, interferons, erythropoietin, or colony stimulating factors), peptide hormones, and fragments thereof.

These proteins may be modified, e.g., to produce variants and fragments of the proteins, as long as the desired biological property (i.e., the ability to bind to the target site) is retained. The proteins may be modified by using various genetic engineering or protein engineering techniques. Another type of modification involves chemically modifying targeting proteins to effect a shift in the isoelectric point of the resulting "charge modified" protein, as described in co-pending U.S. patent application Ser. No. 157,273, entitled "Alteration of Pharmacokinetics of Proteins by Charge Modification". The serum half-life, biodistribution, immunogenicity, and other properties of targeting proteins may be altered by modifying the charge of the protein.

In one embodiment of the invention, the targeting protein is a monoclonal antibody or monoclonal antibody fragment. A number of monoclonal antibodies (MAbs) that bind to a specific type of cell have been developed, including MAbs specific for tumor-associated antigens in humans. Among the many such MAbs that may be used are anti-TAC, or other interleukin-2 receptor antibodies; 9.2.27 and NR-ML-05 to the 250 kilo-dalton human melanoma-associated proteoglycan; NR-LU-10 to 37-40 kilodalton pancarcinoma glycoprotein; and OVB3 to an as yet unidentified tumor-associated antigen. Antibodies derived through genetic engineering or protein engineering may be employed as well. The antibody employed in the present invention may be an intact molecule, a fragment thereof, or a functional equivalent thereof. Examples of antibody fragments are $F(ab')_2$, Fab', Fab, and Fv fragments, which may be produced by conventional methods, or by genetic or protein engineering. Engineered antibodies referred to as single chain antibodies also may be used.

Targeting proteins serve to deliver the effector moiety to a desired target site in vivo. An example of such a target site is a tumor. However, targeting proteins are rarely completely specific for the target tissue, and a portion of an administered conjugate commonly localizes on one or more non-target tissues through such mechanisms as cross-reactive binding and non-specific uptake, including uptake into excretory organs such as the liver and kidneys. The conjugate that becomes localized on non-target tissue comprises the effector moiety bound to either the targeting protein or a degradation product thereof (e.g. a polypeptide fragment of the protein).

The presence of a therapeutic effector moiety localized to a non-target site can cause undesirable side effects and lower the therapeutic index of the immunoconjugate. For example, if the effector moiety is a cytotoxic drug or cytotoxic radionuclide, the presence of high concentrations of the effector moiety localized in a non-target normal tissue can be quite toxic to that tissue.

If the localized non-target site is the kidney, which is often the case when an antibody fragment or other relatively small protein is used as the targeting protein, then the presence of an isotope emitting radiation in high concentrations could cause a dose-limiting toxicity. Additionally, when the targeting protein is a murine whole antibody or serum protein administered to humans, the conjugate often localizes in the liver. The liver tissue thus is exposed to the cytotoxic effects of the therapeutic effector moiety.

The presence of conjugates comprising diagnostic effector moieties at non-target sites may reduce the accuracy of diagnostic procedures. For example, non-target organs having the effector moiety bound thereto may block the detection of target sites during diagnostic imaging procedures. This may be especially true for relatively large non-target organs such as the liver.

In accordance with the present invention, the problems associated with localization of the conjugates at non-target sites can be reduced by separating the effector moiety of the conjugate from the targeting protein by cleaving the linker holding the conjugate together. Cleavage of the linker occurs preferentially at the non-target site and leaves the effector moiety at relatively high concentration at the target site. The result is the excretion of the effector moiety and the continued retention of the targeting protein or degradation products thereof, at the non-target or excretion organ. This effects a reduction of cytotoxic effects on the non-target organ when the effector moiety is a cytotoxic agent, or a reduction of background when the effector moiety is an imaging agent.

In accordance with the present invention, a conjugate comprising a particular targeting protein also comprises a linker through which an effector moiety is attached to the protein, wherein the linker is cleavable under conditions present or induced at one or more non-target sites at which the targeting protein localizes. Thus, a particular linker is chosen for use in view of the biodistribution properties of the particular targeting protein component of the conjugate. The non-target sites at which a particular targeting protein localizes are determined, and a linker is chosen accordingly.

The non-target organ localization patterns of certain types of targeting proteins (e.g., certain types of antibodies and fragments thereof) are known, as discussed above. The biodistribution patterns of other targeting proteins may be established using conventional procedures. e.g. in vivo studies in animals and humans. Problematic non-target organ localization also may be identified during clinical trials. A linker then is chosen for use, wherein the linker is cleavable under conditions present or capable of being induced at one or more of the non-target sites at which the targeting protein of interest localizes. The conditions at the non-target site which promote cleavage of the linker may be the pH, enzymes, reducing agents, or other conditions associated with the particular non-target site.

Alternatively, conditions under which the linker cleaves may be induced at a non-target site. One method by which the conditions present at a non-target organ can be changed involves administering to the patient a cleaving agent capable of changing the conditions present at a non-target site, thereby promoting cleavage of a linker, wherein the linker chosen for use is cleavable under the new conditions induced by the agent. The administered cleaving agent may, for example, be a reducing agent, an oxidizing agent, an enzyme, or a compound that changes the pH at a non-target site. The cleaving agent may act on the linker directly to cause cleavage thereof, e.g., when the cleaving agent is an enzyme and the linker functions as a substrate of the enzyme. Other cleaving agents change the conditions (e.g. the pH) present at one or more non-target sites, wherein the linker is cleaved under the new conditions.

Conjugates administered to a human or mammalian host may bind to a cell surface or the conjugate may be internalized into a cell, depending on such factors as the particular targeting protein in the conjugate. Certain linkers are cleavable intracellularly, e.g., are cleaved by intracellular enzymes or at the acidic pH to which the linker is exposed in endosomes during transport into the cell. Radionuclides, or chelates of radionuclides, released from conjugates inside a cell (including non-target cells) may return to the host's bloodstream, followed by clearance from the body.

In one embodiment of the invention, the cleaving agent is a compound that lowers the pH at the non-target site, generally to an acidic pH. When the non-target organs are the kidneys, the urine can be acidified by conventional procedures involving administration of any of a number of substances known to lower the pH of urine (which normally has a pH near neutrality, i.e., a pH of about 6 to 8). An example of a urine acidifying agent useful as a cleaving agent is ammonium chloride, administered intravenously. If desired, two or more different acidifying agents may be used. For example, methenamine mandelate may be administered to further reduce the pH of acidified urine, as described below. When a urine acidifying agent is to be used as the cleaving agent, a linker susceptible to cleavage at an acidic pH is used to form the conjugate to be administered. The acid cleavable linker will cleave in the more acidic environment of the kidney/urine and not be affected when circulating in the bloodstream.

Any of a number of acid-cleavable linkers may be used. The pH to which the urine pH must be lowered to cleave the linker will vary according to the particular linker used. Examples of such linkers are described in U.S. Pat. Nos. 4,569,789 and 4,631,190, both of which are hereby incorporated by reference, and by Blattler et al. in *Biochemistry*, 24: 1517-1524 (1985). Another type of linker cleavable at acidic pH (including mildly acidic pH) is described in co-pending U.S. patent application Ser. No. 127,656, filed on Dec. 2, 1987, entitled, "Cleavable Immunoconjugates for the Delivery and Release of Agents in Native Form", which is incorporated by reference herein. The linkers described in USSN 127,656 are of the following formula:

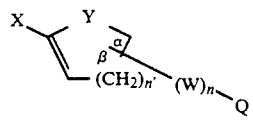

where:
Q is a chemically reactive moiety (i.e., a protein conjugation group);
W is a methylene, methylenoxy, or methylenecarbonyl group or combination thereof;
n is 0 to 10;
Y is an O, S, or NR', wherein R' is an alkyl group of $C_6$ or less;
n' is 1 to 2; and
X is an H, alkyl group of $C_6$ or less, or alkoxy group of $C_6$ or less.

An effector moiety comprising an available nucleophilic group is reacted with the linker whereupon the effector moiety is covalently bound to the linker by addition to the carbon-carbon double bond of the linker ring. Examples of available nucleophilic groups include free sulfhydryl, free amino, and free hydroxyl groups. If the effector moiety does not naturally comprise an available nucleophilic group, it may be synthesized (or derivatized with commercially available derivatizing agents) to contain such a group.

The protein conjugation group Q is a group that will react with a group on a targeting protein to attach the linker thereto. Protein conjugation groups are discussed further below. Conjugates formed using these linkers are represented by the following formula:

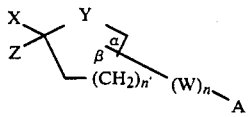

where:
A is an antibody or other targeting protein or fragment thereof; Z is the effector moiety; and the other symbols are as described above.

The linkers in these conjugates are cleavable at mildly acidic pH (e.g., they are effectively cleaved at a pH of about 5). Cleavage of the linker releases the effector moiety in its native form (i.e., without the linker attached thereto.)

Linkers containing esters also may be used in conjunction with cleaving agents that lower the pH of urine. The activity of esterases in the kidney is enhanced at the more acidic pH, and the linkers in conjugates localized at the kidneys therefore are more efficiently cleaved when a urine-acidifying agent is administered.

In another embodiment of the invention, the cleaving agent is a compound that raises the pH at the non-target site, generally to a basic pH. When the non-target organs are the kidneys, the pH of urine can be increased by such methods as the intravenous administration of a salt of ascorbate (e.g., sodium ascorbate) or a bicarbonate salt, such as sodium bicarbonate. The administration of these compounds as the cleaving agent will substantially affect only urine pH because the buffering capacity of blood modulates any pH changes within a narrow range (generally 7.3–7.5) in the blood. Also, the selective excretion of base in urine serves to regulate the pH. The linker chosen for use is a linker susceptible to cleavage under basic pH conditions. The result of an immunoconjugate comprising a base cleavable linker localizing to the kidney will be the excretion of kidney localized effector moiety upon the intravenous administration of these cleaving agents, without substantial cleaving of the circulating immunoconjugate or immunoconjugate localized to the target site. Linkers cleavable at basic pH include, but are not limited to, linkers containing disulfide bonds or esters.

Linkers comprising ester groups also may be susceptible to cleavage by naturally occurring esterases in vivo. Certain ester-containing linkers may be cleavable by circulating plasma esterases (e.g., cholinesterase). For example, linkers may be derived from ester-containing molecules that are susceptible to hydrolysis in plasma, including certain derivatives of glycolamides (2-hydroxy-acetamides) such as those described by Bundgaard and Nielsen in *J. Med. Chem.* 30 (3), 451–454, 1987, which is hereby incorporated by reference. These molecules may be modified for use as linkers, e.g., by attaching groups that are reactive with effector moieties and targeting proteins at the termini of the molecules. Examples of such linkers are those of the following formula:

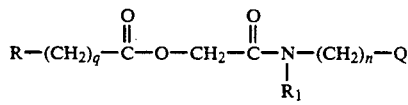

wherein R represents a conjugation group useful for attaching an effector moiety to the linker, $R_1$ is hydrogen or a lower alkyl or substituted lower alkyl group, Q is a protein conjugation group, q is from 0 to about 5, m is 1 or 2, and n is at least 2, preferably from 2 to about 5. The lower alkyl groups generally comprise from 1 to about 6 carbon atoms. Suitable substituents on the alkyl groups include hydroxyl or amine groups, among others. The choice for q depends in part on the effector moiety and whether a longer methylene chain (i.e., a higher value for q) would reduce steric hindrance during the reaction of the particular effector moiety with the linker. When the effector moiety and linker are synthesized as a single molecule, q may represent a smaller integer.

A conjugate comprising a plasma esterase-sensitive linker may be locally injected to the area of the target site or administered by intralymphatic means. Conjugates that diffuse out into the circulation may be cleaved at the ester by the plasma esterases, and the effector moiety removed from the body through renal or hepatic excretion. Locally or intralymphatically administered conjugates may comprise linkers that are quite susceptible to cleavage (i.e., very labile). Alternatively, an ester-containing linker that is not efficiently cleaved in the blood-stream may be susceptible to cleavage by esterases at a non-target organ (e.g., esterases in the kidney or liver). The conjugates comprising such linkers may be administered intravenously, since the relative stability of the linker in serum permits the intact conjugate to reach the target cells in vivo.

In one embodiment of the invention, linkers derived from glycolamides are used to form conjugates of the invention, wherein the linkers comprise esters and are sufficiently stable for intravenous administration to a patient. Examples of such linkers are those of the following general formula:

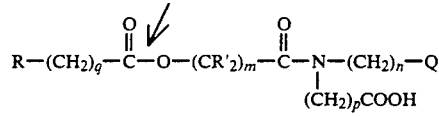

wherein Q represents a protein conjugation group, m is from 1 to about 6, preferably 1 or 2, n is at least about 2 (preferably 2 to 5), q is from 0 to about 5 (as described previously) and p is from 1 to about 4, preferably 1 to 2. R represents a group that will react with an effector moiety to join the linker thereto. Each R' is independently selected from hydrogen and a lower alkyl group, wherein at least one (preferably one or two) R' substituents are lower alkyl groups that each comprise from 1 to about 6 carbon atoms, preferably 1 to 2 carbons. Alternatively the linker and effector moiety may be chemically synthesized as a single molecule, in which case R represents the effector moiety joined to the linker. Among the effector moieties that may be joined to a targeting protein through such linkers are the radionuclide metal chelates or other radiolabeled molecules described below.

These linkers are susceptible to cleavage at the position indicated by the arrow. When conjugates comprising these linkers localize in the liver or kidney, esterases present in these organs cleave the linker, thereby releasing the effector moiety for clearance from the body. If desired, a cleaving agent that raises the pH of urine to a basic level may be administered to the host to further enhance cleaving of the linker at the kidneys. Alternatively, a urine acidifying agent may be administered to enhance the enzymatic activity of kidney esterases.

Another example of a linker containing an ester which may be used in the present invention is a linker of the formula:

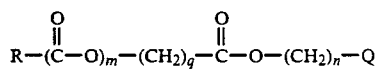

wherein m is 0 or 1, q is 1 to about 3, and n is at least about 2 (preferably 2 to 5). R represents a conjugation group useful for attaching an effector moiety to the linker. Q represents a protein conjugation group which is a functional group that will react with a protein to bind the linker thereto. Protein conjugation groups are further described below. The linker is more labile when q is 1 than when more than one methylene group is positioned between the two ester groups, but these linkers generally are sufficiently stable for intravenous administration of conjugates comprising such linkers.

As discussed above, conjugates comprising radionuclide chelates joined to antibodies through certain ester-containing linkers have been administered in vivo, and clearance of the chelates has been monitored. See, for example, Quadri et al., Haseman et al., and Meares et al., all Supra. Much room remains for improvement in the proportion of chelates that is released by the action of esterases on the particular linkers described by these authors. In accordance with the present invention, a cleaving agent that raises the pH at a non-target site to a basic pH is administered to increase the percentage of these or other ester-containing linkers that are cleaved to release effector moieties from the non-target organ. The above-described cleaving agents that raise the pH of urine may be administered to enhance cleaving of linkers in conjugates localized at the kidneys. Alternatively, urine acidifying agents may be administered to enhance the activity of kidney esterases.

A linker comprising a disulfide bond may be used in conjunction with a cleaving agent that is a compound that raises the pH at a non-target organ. Alternatively, the cleaving agent may be a reducing agent. Compounds that raise the pH of the urine to basic levels have been discussed above, and may be used when the non-target organs are the kidneys.

When the non-target organ is the liver, a linker that cleaves in a high reducing environment can be used to clear effector moieties located in the liver. For example, the relatively high concentration of the reducing agent glutathione that is naturally present in the liver cleaves linkers comprising labile disulfide bonds.

Alternatively, the administration of a cleaving agent that is a reducing agent such as glutathione, cysteine, N-acetyl cysteine, or derivatives thereof effects cleavage of a disulfide bond-containing linker preferentially in the kidneys and/or liver, depending on the biodistribution of the particular reducing agent and the method of administration. Intravenously administered reducing agents may accumulate in the kidneys, whereas orally administered reducing agents such as N-acetyl cysteine accumulate primarily in the liver, but in the kidneys as well.

The disulfide bond should be sufficiently stable to allow the intact conjugate to reach the desired target site in vivo, yet labile enough to be cleavable by a reducing agent at the non-target organ. The stability of a disulfide linker may be increased, if necessary, by attaching one or more "hindering groups" (e.g., methyl or phenyl groups, among others) to the linker near the disulfide bond.

Hindered or stabilized disulfide linkers have been used by Blakey and Thorpe (*Antibody, Immunoconjugates, and Radiopharmaceuticals*, Vol. 1, No. 1, pp 1–17 [1988]) to join the A-chain of ricin (a protein toxin) to a whole antibody. The hindering groups may be inserted within the linker chain or may be substituents attached to the chain. Linkers comprising hindered disulfides may be represented by the following formula:

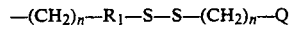

wherein each n represents an integer from 1 to 10, preferably from 1 to about 4; Q represents a protein conjugation group; and $R_1$ represents either a phenyl ring (a hindering group) or

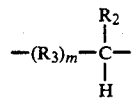

wherein $R_2$ is a methyl group or phenyl ring (hindering group), $R_3$ is a phenyl ring, and m represents an integer from 0 to 1.

For example, a hindered disulfide linker may comprise one of the following structures, among others:

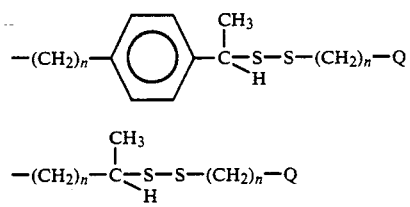

wherein n is from 1 to about 4. The phenyl and methyl groups increase the stability of the disulfide bond. The hindered disulfide provides improved serum stability of the conjugate and thus permits more selective cleavage in nontarget organs where conditions may be altered and/or administered agents can be accumulated.

Linkers that are susceptible to cleavage by an enzyme naturally present in a non-target organ may be used in the present invention. Examples include the esterase-cleavable linkers described above. Alternatively, an enzyme may be administered to the host as a cleaving agent. The enzyme may be one that is not naturally found in the host. Any enzyme that reduces the amount of effector moiety localized at one or more non-target organs by cleaving a linker to release the effector moiety may be used. For example, an enzyme that is cleared from the body through the kidneys may be used. The conjugate administered to the patient comprises a linker that is cleavable by the enzyme, and cleavage of the linker thus occurs at the kidneys.

In one embodiment of the invention, the cleaving agent is a proteolytic enzyme (i.e., a protease) and the linker is an oligopeptide that serves as a substrate for the enzyme (i.e., is cleaved by the proteolytic enzyme). The protease should not be an enzyme that harms the host by degrading essential proteins within the host, e.g., in the host's bloodstream.

The present invention provides conjugates of the formula:

R—L—P wherein R represents an effector moiety; P represents a targeting protein or a protein conjugation group; and L represents an oligopeptide linker that is cleaved by a non-human serine protease.

One proteolytic enzyme that may be used is a serine protease that cleaves substrates having an available histidine residue (i.e., a histidine residue that is exposed in a position that allows binding of the serine protease to the substrate). This non-human enzyme is a mutant of subtilisin that was produced by protein engineering techniques.

The mutant serine protease was derived by changing a histidine residue in subtilisin (amino acid number sixty-four) to an alanine residue. This histidine residue, together with serine at position number 221 and aspartic acid at position number 32, forms the active site of subtilisin. The mutant serine protease requires an available histidine residue in a substrate for enzymatic activity. The mutant enzyme is inactive on normal subtilisin substrates, but will cleave a polypeptide (or fragment thereof) at the amide bond located one residue C-terminal to a histidine residue, if this bond is not between proline residues.

In accordance with the present invention, an oligopeptide linker that is used in conjunction with this mutant serine protease comprises a histidine residue in a position that results in recognition of the linker as a substrate and cleavage of the linker by the protease. The enzyme is expected to be cleared from the body through the kidneys and to cleave a substantially higher percentage of the linker in conjugates localized in the kidneys than conjugates localized at a target site such as a tumor.

A number of oligopeptide linkers comprising histidine residues (wherein the two residues immediately C-terminal to the histidine are not both proline residues) may be used. Preferably, the linker is at least ten amino acid residues in length, contains no proline residues, forms no secondary structure, and advantageously comprises two or three histidines about three or more residues apart. One example of a suitable linker is an oligopeptide having the following amino acid sequence:

-thr-val-asn-his-tyr-arg-thr-val-asn-his-tyr-arg-

Conjugation groups, one for reaction with an effector moiety and the other for reaction with a protein, may be attached at opposite termini of the linker.

In another embodiment of the invention, redox inorganic chemistry is used to release an effector moiety. When a conjugate comprising certain radionuclide metal chelates attached to a targeting protein is localized on the kidneys, a cleaving agent that raises the pH of urine may be administered to promote the release of the radionuclide metal from the chelate compound. Release of the radionuclide metal occurs through cleaving of the bonds between the radionuclide metal and the donor atoms in the chelate compound. Oxidation is believed to cause cleaving of these bonds, and the basic pH conditions induced in the kidneys by administering the cleaving agent enhance this oxidation process.

The effectiveness of this approach for releasing the effector moiety depends on such factors as the oxidation potential of the radionuclide and the chemical structure of the chelate compound. One example of this embodiment of the invention involves a chelate in which a radionuclide metal selected from $^{188}$Re and $^{186}$Re is bound to four donor atoms (three nitrogen donor atoms and one sulfur donor atom) in an "N$_3$S" chelate of the following structure:

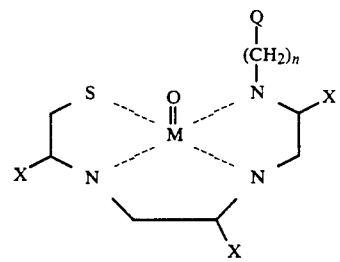

wherein M is a radionuclide of rhenium (e.g., $^{188}$Re or $^{186}$Re), Q is a protein conjugation group, n is an integer of from about 2 to 4, and each X group independently is chosen from oxygen (i.e., $=$O) and H$_2$. The substituent —(CH$_2$)n—Q may be positioned on one of the carbon atoms rather than on the nitrogen atom as shown above. This N$_3$S chelate compound is described in more detail below.

In general, increasing the number of "X" substituents that are oxygen increases the stability of the chelate (i.e., the stability of the bonds holding the radionuclide within the chelate). The number of "X" substituents that are oxygen should be chosen so that the chelate is sufficiently stable to deliver the radionuclide to the target site while being sufficiently labile to permit release of the radionuclide at a non-target site. Preferably, only one or two X substituents are oxygen.

When conjugates comprising such chelates localize on the kidneys, one of the above-described cleaving agents that raise the pH of urine to a basic level is administered to the host. The basic pH conditions promote release of the radionuclide from the chelate. In this particular embodiment of the invention, "cleaving of the linker" means cleaving of the covalent bonds between the radionuclide metal and the donor atoms of the chelate compound. The bonds are cleaved due to oxidation, which is enhanced at basic pH. The radionuclide metal is thereby released and is cleared from the host's body.

Loss of Re-186 or Re-188 from radiolabeled antibodies (antibodies having a rhenium radionuclide metal chelate attached thereto) at elevated pH has been observed. Thus, while stable at pH 7.4, challenges with carbonate buffer at pH 10 resulted in loss of radioactive rhenium. The effect has been greater for Re-186/-188 than Tc-99m which is consistent with the greater oxidation potential of reduced rhenium compared to technetium. Use of triamide thiolate (N$_3$S) chelates has resulted in more loss of rhenium at lower (but still basic) pH than diamide dithiolate (N$_2$S$_2$) chelates. Comparisons at the same elevated pH showed more rapid release of rhenium from the N$_3$S chelates.

Slow loss of Re from radiolabeled antibodies has been observed at pH 7.4 in the presence of phosphate buffered saline. This loss has been markedly reduced by serum, serum albumin, and the chelating agent DTPA. These stabilizers suggest that trace metals may catalyze oxidation of the rhenium to perrhenate (which does not form stable complexes) since chelation of metals such as iron by DTPA or other stabilizers may interfere with the oxidation process.

Perrhenate is excreted predominantly in the urine, even to a greater extent than Tc-99m pertechnetate. Thus, release of Re-186/-188 as perrhenate in the kidney can be expected to result primarily in excretion in the urine.

The linker chosen for use in the present invention may be one that is selectively cleavable at the non-target organ i.e., the linker cleaves under conditions that are present (or induced by the cleaving agent) at the non-target organ to a greater degree than in target tissues. For example, when a base-cleavable linker is used, the agent administered to raise the pH of urine promotes selective cleavage of the linker in the kidneys. The agent advantageously does not raise the pH at the target site of interest, so that the effector moiety remains bound to the target site.

"Selective cleavage" at the non-target tissue means that the linker cleaves only at one or more non-target tissues, or at least to a greater degree compared to the target tissue. Such selective cleavage is especially desirable when it is important that the effector moiety remain attached to the targeting protein at the target site (e.g., when the effector moiety is a diagnostic agent).

Alternatively, cleavage of the linker at both a non-target site and the target site may be desirable when a particular therapeutic effector moiety is more biologically active when released from the targeting protein. While therapeutic radionuclides exert a cytotoxic effect without being taken into target cells, certain agents (e.g., drugs) may be more therapeutically effective when released from the targeting protein (due to release per se, so the drug is in its native form, or the internalization that may follow).

In such cases, a linker may be chosen which is cleavable under conditions which are present, or may be induced, at both the target sites and a non-target organ. For example, an acid cleavable linker which cleaves in the acidic environment of a tumor cell target site may be used so that a therapeutic agent is released from an antibody at the tumor site. Thus, the immunoconjugate need not bind to every cell and need not internalize to be effective. Alternatively, if the immunoconjugate does internalize, the acidic environment of the receptosome/endosome/lysosome will release the effector moiety into the cell. Cleavage of the linker at the kidneys (non-target organs) may be accomplished by acidification of the patient's urine, as described above.

Each of the above-described cleavable linkers may be used to attach a variety of effector moieties to targeting proteins. In one embodiment of the invention, the effector moiety is a diagnostic agent. Any suitable known diagnostic agent may be employed, including but not limited to diagnostic radionuclides such as $^{99m}$Tc, $^{97}$Ru, $^{111}$In, $^{113}$In, $^{123}$I, $^{76}$Br, $^{203}$Pb, $^{18}$F, or $^{64}$Cu; nuclear magnetic resonance imaging contrast agents; X-ray contrast agents; and other diagnostic imaging agents. These agents are detectable by external means (i.e., non-invasive means).

In another embodiment of the invention, the effector moiety is a therapeutic agent. Suitable therapeutic agents include therapeutically effective radioisotopes and therapeutic drugs (including but not limited to anticancer drugs). Therapeutic radioisotopes include, among others, $^{188}$Re, $^{186}$Re, $^{212}$Pb, $^{212}$Bi, $^{109}$Pd, $^{67}$Cu, $^{131}$I, $^{211}$At, $^{105}$Rh, $^{198}$Au, $^{199}$Au and $^{77}$Br. Examples of cytotoxic or antineoplastic drugs are methotrexate; pyrimidine analogs, such as fluorouracil and deoxyuridine; cytosine arabinoside, purine analogs, such as thioguanine, mercaptopurine and azathiopurine; vinca alkaloids, such as vincristine and vinblastine; actinomycin D; daunorubicin, doxorubicin, and other anthracycline derivatives; bleomycin; mitomycin; L-asparaginase; platinum derivatives; and nitrogen mustards such as L-phenylalanine nitrogen mustard and cyclophosphamide.

The radionuclides (whether diagnostic or therapeutic) generally are bound by a binding molecule. For example, the radionuclide may be in the form of a stable complex such as a chelate, which may be prepared by known methods. Another type of binding molecule is a small molecule to which a radionuclide may be stably bound by a single covalent bond.

A number of chelating compounds (or radionuclide metal chelates derived therefrom) may be attached to targeting proteins using the above-described cleavable linkers. Among the known chelating compounds are the diamide dimercaptide (N$_2$S$_2$) compounds which are used to chelate various metal radionuclides having diagnostic or therapeutic use. (See European Patent Application publication number 188,256 or U.S. Pat. Nos. 4,444,690 and 4,670,545, which are hereby incorporated by reference). Compounds known as N$_3$S chelating compounds also may be used. (See Fritzberg et al. *J. Nucl. Med.* 27:1, 1986 and European Patent Application publication number 173,424, which are hereby incorporated by reference). Another known chelating compound is diethylenetriaminepentaacetic acid (DTPA), described by Fritzberg (*J. Nuc. Med. Tech.* Vol. 12, No. 4, December 1984) and in U.S. Pat. No. 4,652,440. Additional radionuclide metal chelate compounds are described in U.S. Pat. Nos. 4,287,362; 4,421,735; and 4,678,667. Other chelating compounds having a variety of chemical structures are known and may be attached to targeting proteins through one of the above-described linkers.

In one embodiment of the invention, the chelating compound comprises a total of at least four donor atoms selected from nitrogen and sulfur donor atoms. Donor atoms are atoms that form bonds to the metal radionuclide to form the chelate. One example of such a chelating compound is an "N$_2$S$_2$" chelating compound that comprises two nitrogen donor atoms and two sulfur donor atoms, such as a compound of the following formula:

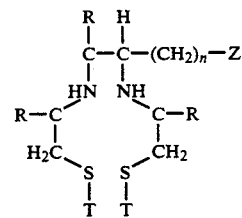

wherein n is from 1 to about 4 (preferably 2); Z represents a conjugation group (for reaction with a cleavable linker of the present invention); each R independently is selected from ═O and H$_2$; and T represents a sulfur protecting group.

Compounds of this formula are among those described in European Patent Application publication number 188,256 and in co-pending U.S. patent application Ser. No. 065,017, filed Jun. 19, 1987, entitled "Metal Radionuclide Labeled Proteins for Diagnosis and Therapy", both of which are incorporated by reference in their entirety.

T represents any suitable sulfur protecting group and each T may represent the same, or a different, protecting group. Preferably, each T represents a protecting group that, when taken together with the sulfur atom to which it is attached, forms a hemithioacetal group of the formula:

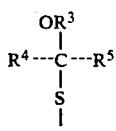

wherein $R^3$ is a lower alkyl group, preferably of from two to five carbon atoms, and $R^4$ is a lower alkyl group, preferably of from one to three carbon atoms. Alternatively, $R^3$ and $R^4$ may be taken together with the carbon atom and the oxygen atom shown in the formula to define a nonaromatic ring, preferably comprising from three to seven carbon atoms in addition to the carbon and oxygen atoms shown in the formula. $R^5$ represents hydrogen or a lower alkyl group wherein the alkyl group preferably is of from one to three carbon atoms. Examples of such preferred hemithioacetals include, but are not limited to:

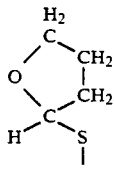

Tetrahydrofuranyl

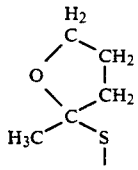

2-methyl tetrahydrofuranyl

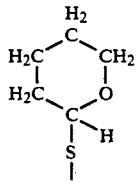

Tetrahydropyranyl

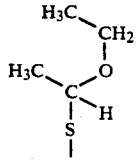

ethoxyethyl

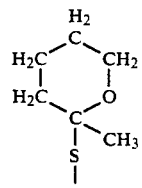

2-methyl tetrahydropyranyl

Other hemithioacetal sulfur-protecting groups may be derived from sugars such as monosaccharides. In one embodiment of the invention, the sulfur protecting group is a monosaccharide comprising five or six carbon atoms, or a derivative thereof. The use of these sulfur protecting groups enhances the water solubility of the chelating compound. Examples of such protecting groups are as follows, where the sulfur donor atoms of the chelating compound to which the protecting group is attached also is shown:

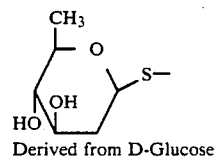

Derived from D-Glucose

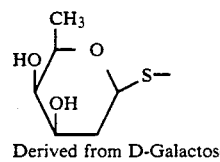

Derived from D-Galactose

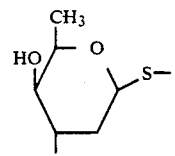

Derived from L-Rhamnose

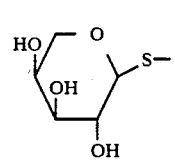

Derived from D-Xylose

The $N_2S_2$ chelating compound may be radiolabeled before or after attachment to the targeting protein to produce a radionuclide metal chelate of the formula:

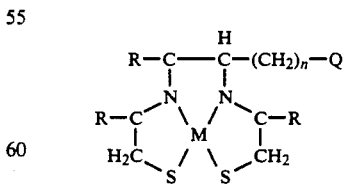

wherein M represents a radionuclide metal or an oxide thereof, and the other symbols are as described above.

Another example of a chelating compound that may be used is an "$N_3S$" compound comprising three nitrogen donor atoms and one sulfur donor atom, such as a compound of the following formula:

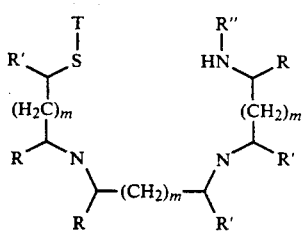

wherein:
T is a sulfur protecting group (with S-T preferably representing a hemithioacetal group, as described above for the N₂S₂ compounds);
each R independently represents H₂ or =O;
each R' independently represents a substituent selected from the group consisting of hydrogen, a non-alkyl side chain of an amino acid other than cysteine, geminal dialkyl, and —(CH₂)n—Z;
Z represents —COOH or a conjugation group (for reaction with one of the cleavable linkers described above);
m represents 0 or 1, with the proviso that at most one m represents 1;
n is an integer of from 1 to about 4; and
R" is hydrogen; —(CH₂)n—Z; or an alkyl group having one or more polar groups substituted thereon;
wherein the compound comprises at least one —(CH₂)n—Z.

Radiolabeling of the N₃S chelating compound produces a radionuclide metal chelate of the following formula:

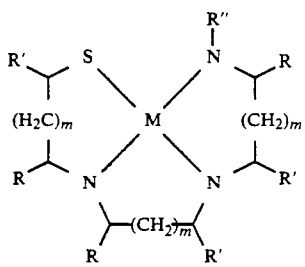

wherein M represents a radionuclide metal or oxide thereof, and the other symbols are as described above.

Methods for synthesizing various N₃S chelating compounds are known. See, for example, European patent application publication number 173,424, and U.S. patent application Ser. No. 172,004, filed Mar. 23, 1988, entitled "Metal-Radionuclide-Labeled Proteins and Glycoproteins for Diagnosis and Therapy", which is hereby incorporated in its entirety by reference.

Other chelating compounds may have different combinations of donor atoms. Such compounds include N₂S₄, N₂S₃, and N₃S₃ chelating compounds, among others.

The chelating compounds are radiolabeled with an appropriate radionuclide to produce the corresponding chelate. The radiolabeling step may be done either before or after the compound is attached to a targeting protein through a cleavable linker, depending on such factors as the structure of the chelating compound and the radiolabeling reaction conditions. Conventional procedures are used for radiolabeling the chelating compounds.

For example, pertechnetate ($^{99m}TcO_4-$) or perrhenate ($^{186}$ or $^{188}ReO_4-$) are generally contacted with a chelating compound in the presence of a reducing agent (e.g., a ferrous or stannous salt or dithionite or electrolytic generation of reducing electrons) to effect reduction of the radionuclide to an oxidation state at which chelation can occur. Alternatively, the pertechnetate or perrhenate may be reduced in the presence of a relatively labile complexing agent such as gluconic acid or citric acid to form intermediate complexes ($^{99m}Tc$-gluconate or $^{188}Re$-citrate). When the intermediate complexes are contacted with the chelating compound under appropriate reaction conditions (which may involve heating), the radionuclide metal is transferred to the chelating compound, thereby producing a stable radionuclide metal chelate.

Chelates of $^{212}Pb$, $^{212}Bi$ and $^{109}Pd$ may be prepared by combining the appropriate salt of the radionuclide with the chelating compound and incubating the reaction mixture at room temperature or at higher temperatures. It is not necessary to treat the lead, bismuth, palladium, and copper radioisotopes with a reducing agent prior to chelation, as such isotopes are already in an oxidation state suitable for chelation. The specific radiolabeling reaction conditions may vary somewhat according to the particular radionuclide and chelating compound involved.

Examples of some of the many possible combinations of radionuclide metal chelate effector moieties and cleavable linkers that are within the scope of the present invention are represented by formulas I to III as follows:

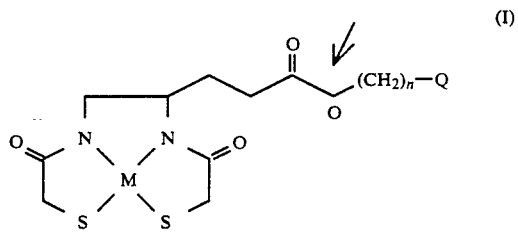

wherein Q represents a protein conjugation group, n represents an integer from 1 to 3, M represents a metal radionuclide or an oxide thereof, including but not limited to oxides of $^{99m}Tc$, $^{188}Re$, or $^{186}Re$, and the ester-containing linker is cleavable in vivo at the position indicated by the arrow.

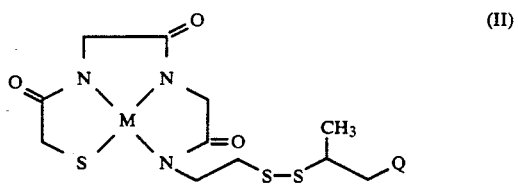

wherein Q represents a protein conjugation group, M represents a metal radionuclide or an oxide thereof, including but not limited to oxides of $^{99m}Tc$, $^{188}Re$, or $^{186}Re$, and the linker comprises a hindered disulfide bond. The linker may comprise a second hindering group (e.g. a phenyl group).

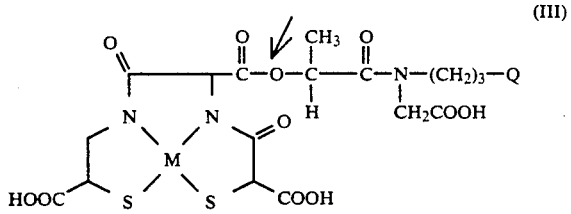
(III)

wherein Q represents a protein conjugation group, M represents a metal radionuclide or an oxide thereof, including but not limited to oxides of $^{99m}Tc$, $^{188}Re$, or $^{186}Re$, and the ester-containing linker is cleavable in vivo at the position indicated by the arrow.

Other chelates may be substituted for those presented in formulas I through III. In addition, the other cleavable linkers presented above (e.g., the peptide linkers, acid-cleavable linkers, other ester-containing linkers, etc.) may be attached to the metal radionuclide chelates.

Other radionuclide binding molecules which may be used include the vinyl group containing compounds described in co-pending U.S. patent application Ser. No. 039,155, filed Apr. 16, 1987 which is hereby incorporated by reference. Representative radiohalogenated small molecules disclosed in U.S. Ser. No. 039,155 are as follows:

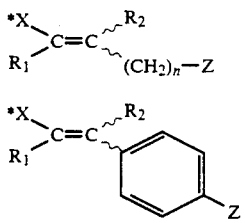

wherein radiohalogen *X is substituted on C=C in either the cis, trans, or geminal (not shown) orientation with respect to substituent Z. The integer "n" is preferably 1 through 3. Z represents a chemically reactive conjugation group used to join these effector moieties to a cleavable linker of the present invention.

Radiohalogens include any radioisotope of: iodine, particularly I-123, I-125, and I-131; bromine, particularly Br-75, Br-76 and Br-77; fluorine, particularly F-18; and, astatine, particularly At-211. Preferred radiohalogens *X for diagnostic imaging purposes include I-131 and most preferably I-123 for imaging with gamma cameras; and for positron tomographic imaging: F-18, Br-75, and Br-76. For clinical radio-therapy, preferred radiohalogens *X include I-131, Br-77, and At-211.

Other binding molecules that bind radiohalogens at the meta or para position on a phenyl ring are described in European Patent Application Publication Number 203,764, which is hereby incorporated by reference. These compounds may be represented by the following formula:

*X—Ar—R wherein
*X is a radioisotope of iodine, bromine, fluorine, or astatine;
Ar is aromatic or heteroaromatic ring;
R is a chemical bond or a substituent containing 1 to 12 straight-chain carbon atoms that does not activate Ar toward electrophilic substitution on the order produced by hydroxy or amino substitution of the ring, wherein said bond or said substituent has attached thereto a functional group suitable for conjugation. *I-para-iodophenyl compounds (in which *I represents a radioisotope of iodine) may be prepared using the procedures described in EP 203,764, which generally involve substituting the organometallic group Sn(n-Bu)$_3$ or SnMe$_3$ on a haloaromatic compound. A radioisotope of a halogen then is substituted for the organometallic group by halodemetalization. Examples of radiohalogenated molecules that may be prepared using such a procedure are represented by the following formulas:

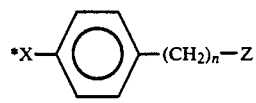

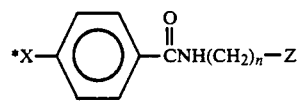

wherein n represents an integer from 0 to 3, Z represents a conjugation group, and *X represents a radioisotope of a halogen.

The linkers used to prepare the conjugates of the invention generally are synthesized or derivatized to comprise a functional group at one terminus that will react with an effector moiety to bind the effector moiety to the linker. The linker generally comprises a second functional group (a protein conjugation group, often at the other terminus of the linker) that will react with a protein to bind the linker to the protein. Alternatively, the linker and effector moiety (or precursor thereof) may be synthesized as a single molecule (e.g., the molecules of formulas I to III above) rather than being synthesized as separate molecules to be joined later. Effector moiety precursors include chelating compounds or other complexing molecules prior to radiolabeling. The functional group will vary according to the type of effector moiety to be attached to the linker. The chemical synthesis procedures will vary according to the chemical structure of the effector-linker molecule.

While certain of the above-described linkers are shown as having a conjugation group at each terminus, it is to be understood that these conjugation groups may not always be present. For example, the linker and effector moiety may be synthesized as a single molecule, in which case the linker need not comprise a conjugation group for reaction with the effector moiety to join the linker thereto. In addition, when a linker is reacted with a targeting protein and an effector moiety to form a conjugate of the invention, the conjugation groups in the linker formulas presented above are replaced by a targeting protein at one terminus and an effector moiety at the other linker terminus. Only a portion of the conjugation groups(s) remains between the three components in the conjugate.

A protein conjugation group is a functional group that will react with a group on a protein under conditions that preserve the biological activity of the protein. Protein conjugation groups include, but are not limited to, esters, including carboxylic esters of the formula COOR (wherein OR is a leaving group), imide esters, imidate esters, phenolic esters, substituted phenolic esters, and thiophenyl esters, Michael-type acceptor groups (e.g., maleimides), free amines, hydrazines, thiols, carboxylate, and isothiocyanate groups. Among the preferred protein conjugation groups which may be used in the present invention are:

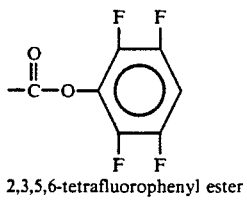

2,3,5,6-tetrafluorophenyl ester

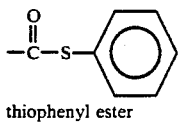

thiophenyl ester and

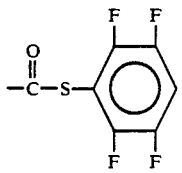

2,3,5,6-tetrafluorophenyl thioester

Proteins contain a variety of functional groups (e.g., carboxylic acid [COOH] or free amine [—NH$_2$] groups), which are available for reaction with a suitable protein conjugation group on a linker molecule to bind the linker thereto. For example, carboxylic esters react with the free (epsilon) amine groups of the lysine residues on a protein to form amide bonds. Alternatively, the targeting protein and/or linker may be derivatized to expose or attach additional reactive functional groups. Derivatization may involve chemical treatment of the protein; e.g., oxidative cleavage of the sugar moiety of a glycoprotein antibody with periodate to generate free aldehyde groups. The free aldehyde groups on the antibody may be reacted with free amine or hydrazine groups on a linker to bind the linker to the antibody (see U.S. Pat. No. 4,671,958). Procedures for generation of free sulfhydryl groups on antibodies or antibody fragments also are known. (See U.S. Pat. No. 4,659,839.) The free sulfhydryl groups may be reacted with a maleimide group on the linking group.

In accordance with the present invention, conjugates comprising an effector moiety attached to a cleavable linker which in turn is attached to a targeting protein are administered to a human or mammalian host for diagnostic or therapeutic purposes, depending on the effector moiety. The conjugate may be administered intravenously, intraperitoneally, intralymphatically, locally, or by other suitable means, depending on such factors as the type of target site. The amount to be administered will vary according to such factors as the type of effector moiety (e.g., its potency and whether it is a diagnostic or therapeutic agent) and the affinity of the targeting protein for the target site of interest. Appropriate dosages may be established by conventional proedures, e.g., animal studies and human clinical trials.

When a cleaving agent also is to be administered to the patient to effect cleavage of the linker, a suitable length of time generally is allowed to pass to allow localization of the conjugate on the target site(s) (and non-target sites) prior to administration of the cleaving agent. For diagnostic procedures, analysis of the biodistribution of the diagnostic agent by conventional procedures (e.g., NMR, X-rays, or scanning the patient with a gamma camera) is preferably delayed until the agent that promotes cleavage of the linker has been administered and substantial clearance of the imaging agent from non-target tissues has occurred. The cleaving agent is administered in an amount effective in reducing the amount of effector moiety that is localized on one or more non-target sites. The amount to be administered will vary according to such factors as the particular linker and cleaving agent to be used (e.g., how efficiently the linker is cleaved), the amount of effector moiety at the non-target site, etc.

For ammonium bicarbonate (a cleaving agent that raises the pH of urine), an amount sufficient to raise the urine pH to about 8.5–9.0 is preferably administered. For relatively stable linkers, a higher pH may be desired. This may be accomplished by hydrating a patient intravenously, adding NaHCO$_3$ to the infusion, and checking the pH of the urine. More NaHCO$_3$ is used until the pH is consistently at the desired level. Methods for altering and monitoring the pH of urine are known. A similar procedure is used for high dose methotrexate with citrovorum rescue in patients.

A urine-acidifying agent (e.g., ammonium chloride) may be administered intravenously by similar procedures until the desired urine pH is achieved. A drug such as mandelamine ® may be administered orally to further reduce the pH if desired. Mandelamine ®, also called methenamine mandelate (the chemical combination of mandelic acid with methenamine) is a known urinary antibacterial agent. The drug is excreted by the kidneys and concentrated in the urine. In acidic urine, mandelamine cleaves to ammonia, formaldehyde and mandelic acid, which causes further acidification.

An example of a reducing agent that may be administered as a cleaving agent is N-acetyl cysteine. This agent is known to accumulate in the liver, and is used for such medical purposes as reduction of liver damage following an overdose of acetaminophen. A smaller portion of the orally administered dose may accumulate in the kidneys.

The reduction in the amount of effector moiety bound to non-target sites that is accomplished using the method of the present invention may allow administration of higher dosages of therapeutic agents. Enhanced therapeutic efficacy thus may be achieved through administration of the higher dosages that are possible when the therapeutic agent can be cleared from non-target organs. Improved accuracy in diagnostic procedures also is expected to result when imaging agents are cleared from non-target tissues using the method of the invention.

The use of conditionally cleavable linkers to reduce accumulation of a targeting protein-effector moiety conjugate in non-target organs generally is most effective when the non-target organ accumulation is due to the targeting protein portion of the conjugate. Certain effector moieties have biodistribution properties that result in non-target site accumulation in vivo. In such cases, release of the effector moiety from the targeting protein would not be expected to result in clearance of the effector moiety from the body, since there are nontarget sites in which the effector moiety per se naturally accumulates.

Among the effector moieties that may accumulate in non-target organs after release from a targeting protein are certain protein toxins that accumulate in the liver. Certain chelate compounds are known to have an affinity for bone or other non-target sites in vivo. Thus, when the effector moiety is a metal radionuclide within a chelate, an important aspect of the success of the present invention is using chelating agents for radionuclide metals such as Tc-99m, Re-186, -88, Ru-97, Rh-105, etc. that form complexes that are not retained by the liver and kidneys. While many Tc-99m complexes are retained to some extent in these organs, the $N_2S_2$ and $N_3S$ chelating agents described above are especially useful in that they are not retained and are excreted via mediated transport in the kidneys.

From the foregoing, it will be appreciated that, although specific embodiments of the invention have been described for purposes of illustration, various modifications may be made without departing from the spirit and scope of the invention. The examples presented below are provided for purposes of illustration, and are not to be construed as limiting the scope of the invention.

What is claimed is:

1. A method for reducing non-target site accumulation of an effector moiety, comprising administering to a human or mammalian host a conjugate comprising an effector moiety attached to a targeting protein through a linker and administering to the host a cleaving agent that effects cleavage of the linker at one or more non-target sites within the host.

2. The method of claim 1 wherein the non-target sites are the kidneys.

3. The method of claim 2 wherein the cleaving agent is a compound that lowers the pH of the host's urine to an acidic pH, and the linker is cleaved at the acidic pH.

4. The method of claim 3 wherein the linker comprises an ester group that is cleaved by esterases in the kidney at acidic pH.

5. The method of claim 3 wherein the cleaving agent is ammonium chloride.

6. The method of claim 5 wherein methenamine mandelate additionally is administered as a cleaving agent.

7. The method of claim 2 wherein the cleaving agent is a compound that raises the pH of the host's urine to a basic pH.

8. The method of claim 7 wherein the cleaving agent is selected from the group consisting of ascorbate salts and bicarbonate salts.

9. The method of claim 7 or 8 wherein the linker comprises at least one ester.

10. The method of claim 9 wherein the linker comprises the following chemical structure:

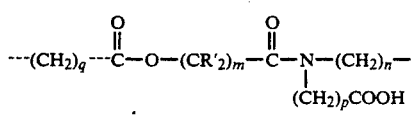

wherein q is 0 to about 5, m is from 1 to 6, n is from 2 to about 5, p is from 1 to about 4, and each R' is independently selected from hydrogen and a lower alkyl group, wherein at least one R' is a lower alkyl group of from 1-6 carbon atoms.

11. The method of claim 9 wherein the linker comprises the following chemical structure:

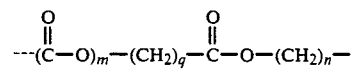

wherein m is 0 or 1, q is from 1 to about 3, and n is from 2 to about 5.

12. The method of claim 7 or 8 wherein the linker comprises a hindered disulfide bond.

13. The method of claim 12 wherein the linker comprises the following chemical structure:

wherein each n represents an integer from 1 to about 4; and $R_1$ represents either a phenyl ring or

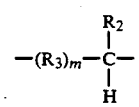

wherein $R_2$ is a methyl group or phenyl ring, $R_3$ is a phenyl ring, and m represents an integer from 0 to 1.

14. The method of claim 2 wherein the cleaving agent is an enzyme that accumulates in the host's kidneys after administration to the host.

15. The method of claim 14 wherein the linker is an oligopeptide and the enzyme is a protease that cleaves said oligopeptide.

16. The method of claim 15 wherein the oligopeptide comprises a histidine residue without two proline residues on the carboxyl-terminal side of the histidine, immediately adjacent to the histidine, and the protease is a serine protease derived from subtilisin by replacing or deleting the histidine residue at position 64 in subtilisin.

17. The method of claim 1 wherein the cleaving agent is a reducing agent, the non-target site is the liver and/or the kidneys, and said reducing agent accumulates in at least one of the non-target sites after administration.

18. The method of claim 17 wherein the reducing agent is selected from the group consisting of glutathione, cysteine, N-acetyl cysteine, and derivatives thereof.

19. The method of claim 17 or 18 wherein the linker comprises a hindered disulfide bond.

20. The method of claim 19 wherein the linker comprises the following chemical structure:

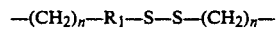

wherein each n represents an integer from 1 to about 4: and $R_1$ represents either a phenyl ring or

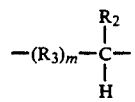

wherein $R_2$ is a methyl group or phenyl ring, $R_3$ is a phenyl ring, and m represents an integer from 0 to 1.

21. The method of claim 1 wherein the effector moiety comprises a diagnostic agent.

22. The method of claim 21 wherein the diagnostic agent is selected from the group consisting of diagnostic radionuclides, nuclear magnetic resonance contrast agents, and X-ray contrast agents.

23. The method of claim 22 wherein the diagnostic radionuclide is selected from the group consisting of $^{99m}$Tc, $^{111}$In, $^{113}$In, $^{123}$I, $^{76}$Br, $^{18}$F, $^{97}$Ru, $^{203}$Pb, and $^{64}$Cu.

24. The method of claim 1 wherein the effector moiety comprises a therapeutic agent.

25. The method of claim 24 wherein the therapeutic agent is a therapeutic radionuclide or a drug.

26. The method of claim 25 wherein the therapeutic radionuclide is selected from the group consisting of $^{186}$Re, $^{188}$Re, $^{212}$Bi, $^{109}$Pd, $^{67}$Cu, $^{131}$I, $^{211}$At, $^{77}$Br, $^{105}$Rh, $^{198}$Au, $^{199}$Au and $^{212}$Pb.

27. The method of claim 22, 23, 25 or 26 wherein the radionuclide is a radionuclide metal in the form of a chelate.

28. The method of claim 27 wherein the radionuclide metal is selected from $^{99m}$Tc, $^{186}$Re, and $^{188}$Re and the chelate comprises a total of four donor atoms selected from nitrogen and sulfur atoms.

29. The method of claim 22, 23, 25 or 26 wherein the radionuclide is a radiohalogen attached by a single bond to a binding molecule.

30. The method of claim 1 wherein the targeting protein is selected from the group consisting of antibodies, hormones, enzymes, biologic response modifiers, and fragments thereof.

31. The method of claim 30 wherein the targeting protein is a monoclonal antibody or a fragment thereof.

32. The method of claim 31 wherein the monoclonal antibody or fragment thereof binds to cancer cells.

33. The method of claim 7 or 8 wherein the effector moiety is a radionuclide metal and the linker comprises a compound that binds the radionuclide metal to form a chelate, wherein the bonds between the radionuclide metal and donor atoms in the chelate are rendered more susceptible to oxidative cleavage at a basic pH.

34. The method of claim 33 wherein the conjugate is of the formula:

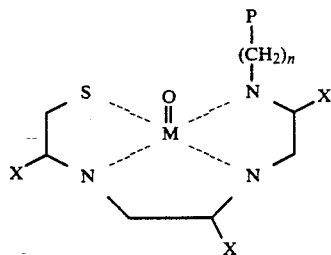

wherein M is a radionuclide of rhenium, P is a targeting protein, n is an integer of from about 2 to 4, and each X group independently is chosen from =O and H$_2$.

* * * * *